US011622747B2

(12) United States Patent
Terada et al.

(10) Patent No.: US 11,622,747 B2
(45) Date of Patent: Apr. 11, 2023

(54) ULTRASONIC CT DEVICE, CONTROL METHOD OF ULTRASONIC CT DEVICE, AND ULTRASONIC TRANSMISSION AND RECEPTION DEVICE

(71) Applicant: Hitachi, Ltd., Tokyo (JP)

(72) Inventors: Takahide Terada, Tokyo (JP); Yushi Tsubota, Tokyo (JP); Atsurou Suzuki, Tokyo (JP); Kenichi Kawabata, Tokyo (JP); Kazuhiro Yamanaka, Tokyo (JP)

(73) Assignee: FUJIFILM HEALTHCARE CORPORATION, Chiba (JP)

( * ) Notice: Subject to any disclaimer, the term of this patent is extended or adjusted under 35 U.S.C. 154(b) by 371 days.

(21) Appl. No.: 16/876,200

(22) Filed: May 18, 2020

(65) Prior Publication Data
US 2021/0228180 A1 Jul. 29, 2021

(30) Foreign Application Priority Data

Jan. 27, 2020 (JP) .............................. JP2020-011093

(51) Int. Cl.
*A61B 8/15* (2006.01)
*G01S 15/10* (2006.01)
(Continued)

(52) U.S. Cl.
CPC .............. *A61B 8/15* (2013.01); *G01S 15/102* (2013.01); *G01S 15/878* (2013.01); *G01S 15/8915* (2013.01)

(58) Field of Classification Search
CPC ....... A61B 8/15; G01S 15/102; G01S 15/878; G01S 15/8915
See application file for complete search history.

(56) References Cited

U.S. PATENT DOCUMENTS

2005/0124891 A1* 6/2005 Amemiya ................ A61B 8/06
600/447
2017/0128038 A1* 5/2017 Tsushima .............. A61B 8/5207
2018/0185005 A1* 7/2018 Sandhu ................... G16H 50/30

FOREIGN PATENT DOCUMENTS

| JP | 2003070788 A | 3/2003 |
| WO | 2017098641 A1 | 6/2017 |

OTHER PUBLICATIONS

Satoshi Tamano et al., "Compensationof transducer element positions in a ring array ultrasonic computer tomography system", Japanese Journal of Applied Physics 54, 07HF24, 2015.

* cited by examiner

*Primary Examiner* — Peter M Bythrow
*Assistant Examiner* — Nazra Nur Waheed
(74) *Attorney, Agent, or Firm* — Mattingly & Malur, PC

(57) ABSTRACT

An object of the invention is to provide an ultrasonic CT device in which a reflected signal or the like from an object disposed close to transducers is received, and a reception signal thereof can be received by a receiver while transceivers whose number is smaller than the number of the transducers are used. The ultrasonic CT device includes: a transducer array in which a plurality of transducers are arranged; transceivers whose number is smaller than the number of the transducers; and a transmission transducer selector and a reception transducer selector disposed for each of the transceivers. While a transmitter included in the transceiver is selectively connected to any of the transducers in the transducer array by the transmission transducer selector, a receiver included in the transceiver is selectively (Continued)

connected to any of the transducers in the transducer array by the reception transducer selector.

13 Claims, 14 Drawing Sheets

(51) Int. Cl.
    *G01S 15/87*         (2006.01)
    *G01S 15/89*         (2006.01)

[FIG. 1]
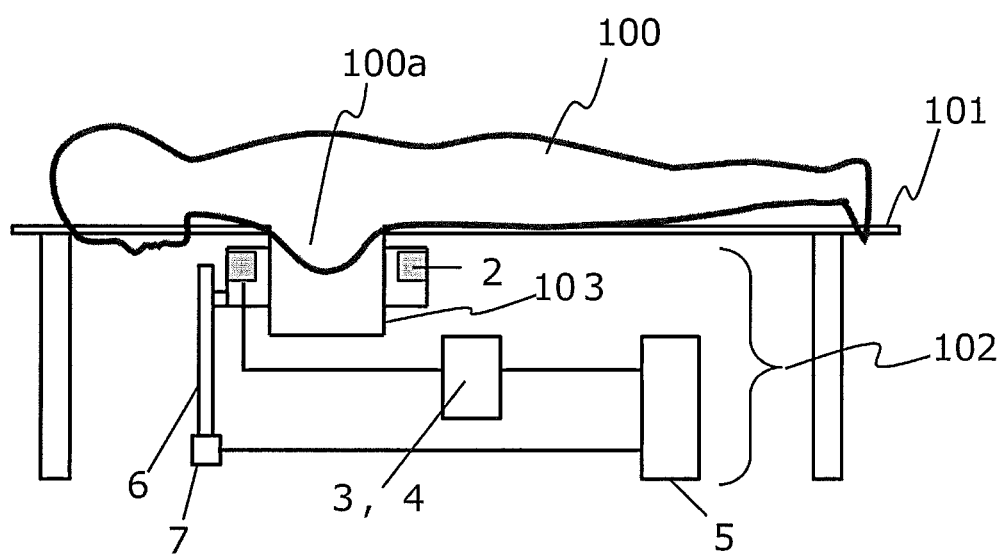

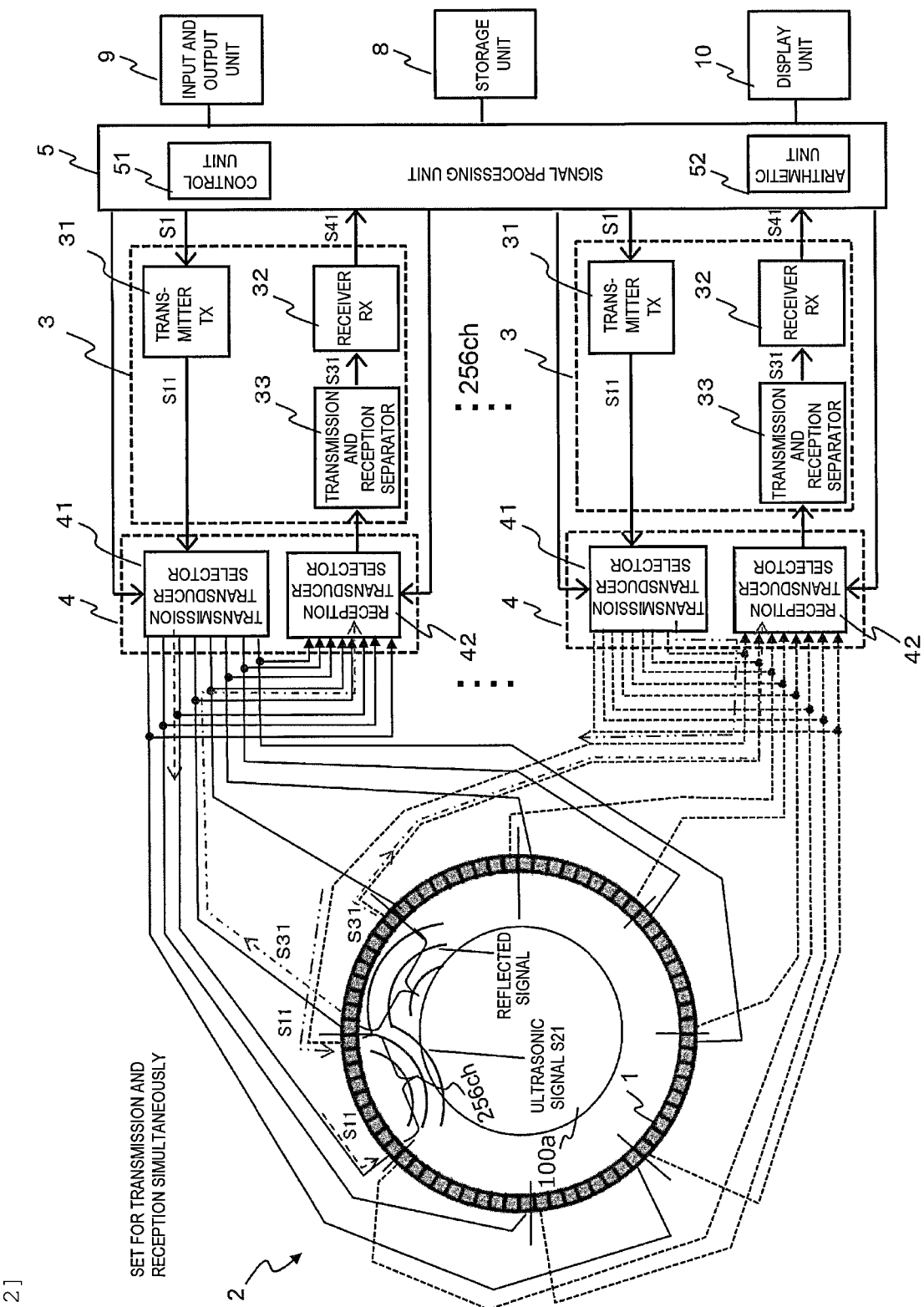
[FIG. 2]

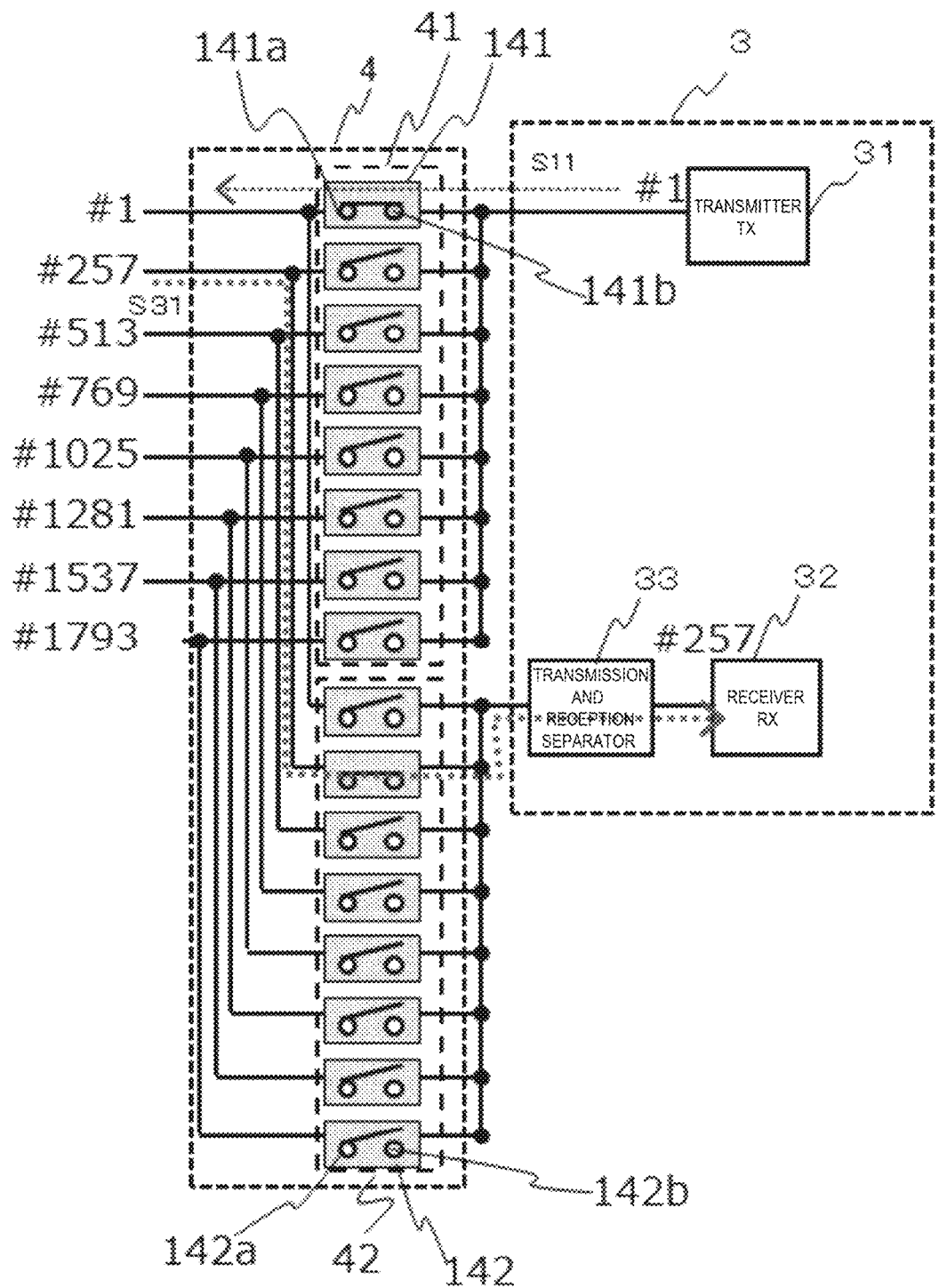
[FIG. 3]

[FIG. 4]
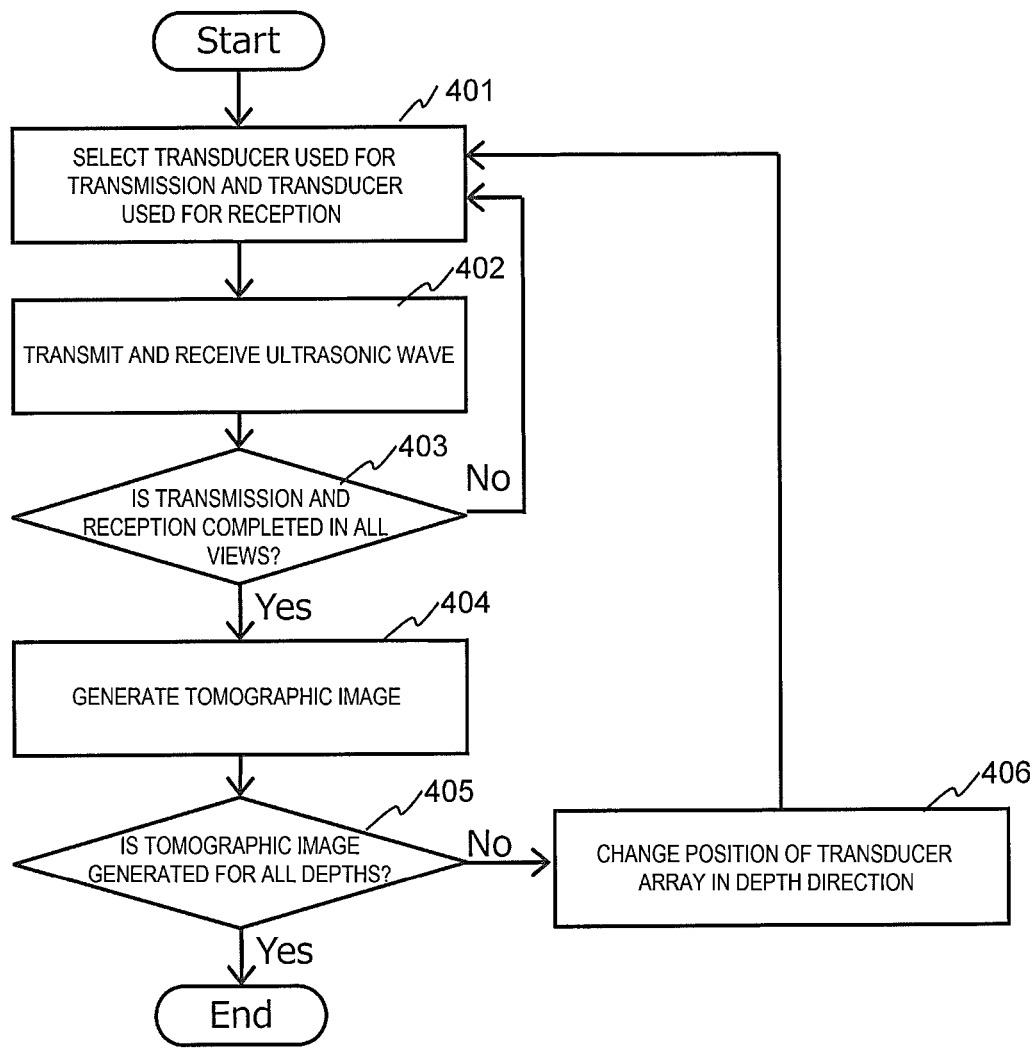

[FIG. 5A]
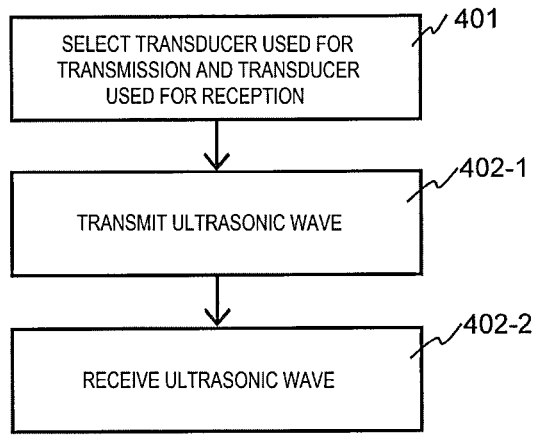
[FIG. 5B]
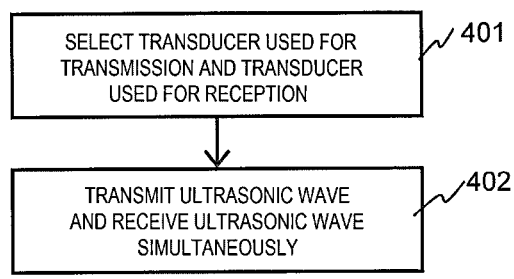
[FIG. 6]
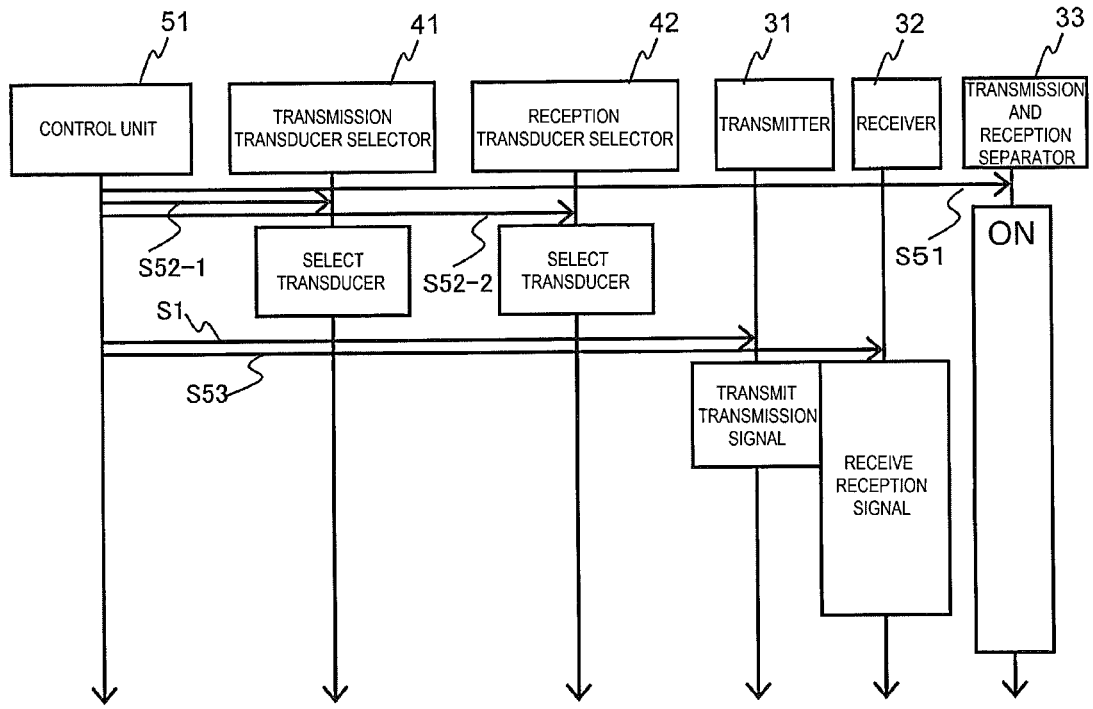

[FIG. 7A]
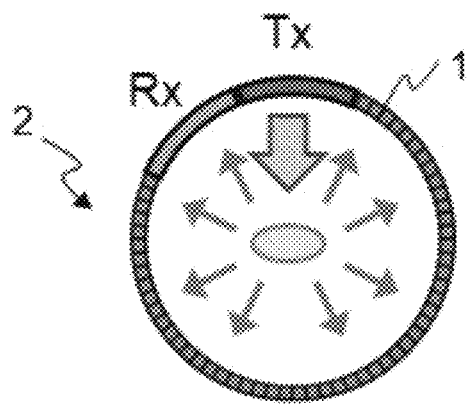
[FIG. 7D]
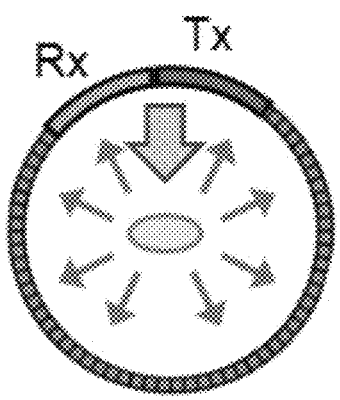
[FIG. 7B]
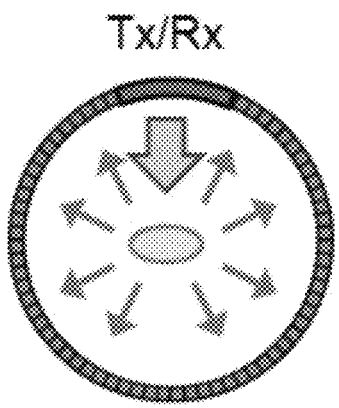
[FIG. 7E]
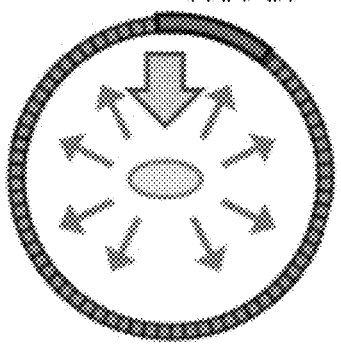
[FIG. 7C]
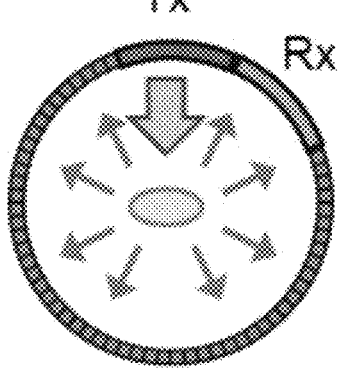
[FIG. 7F]
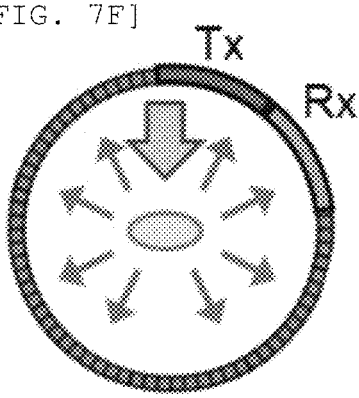

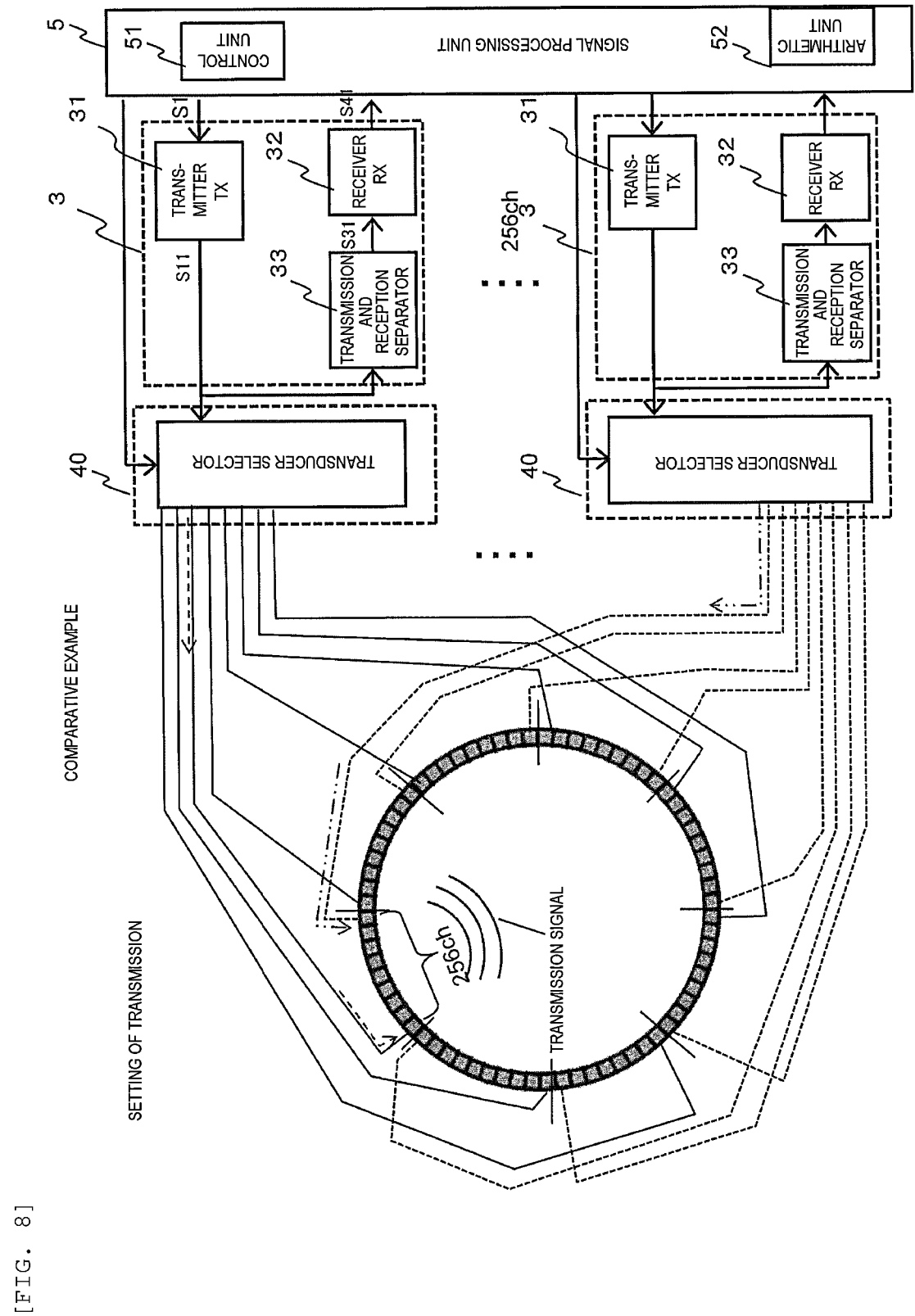
[FIG. 8]

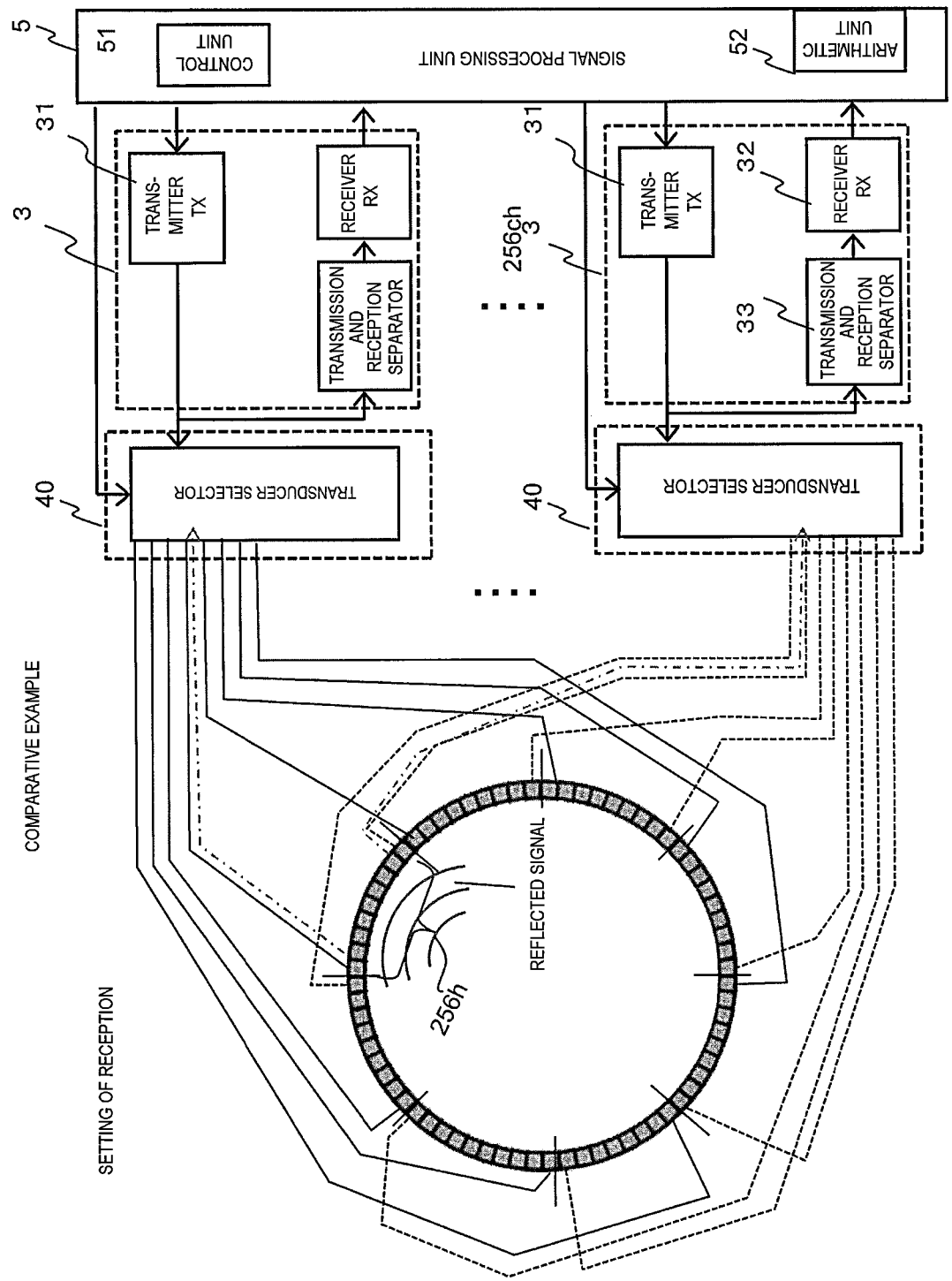
[FIG. 9]

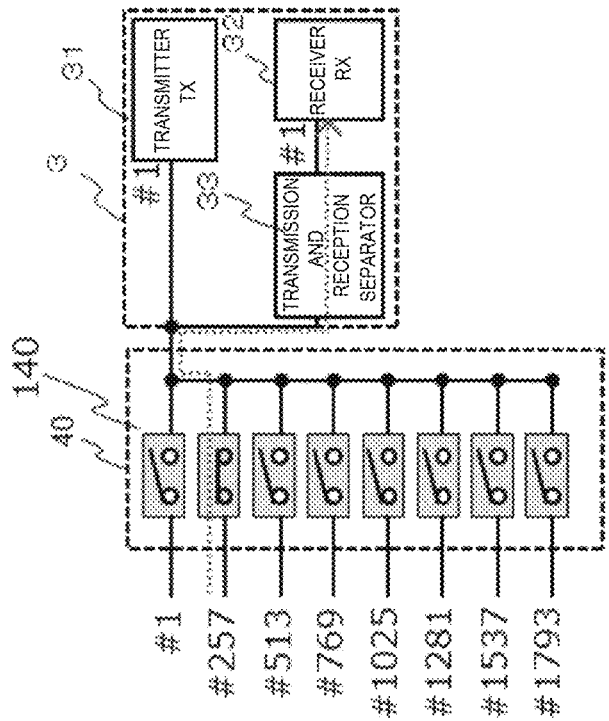
[FIG. 10B]
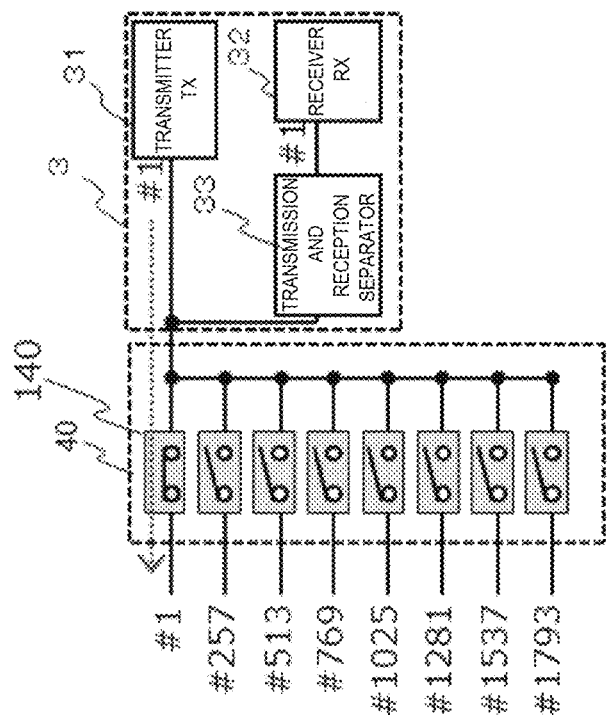
[FIG. 10A]

[FIG. 11]
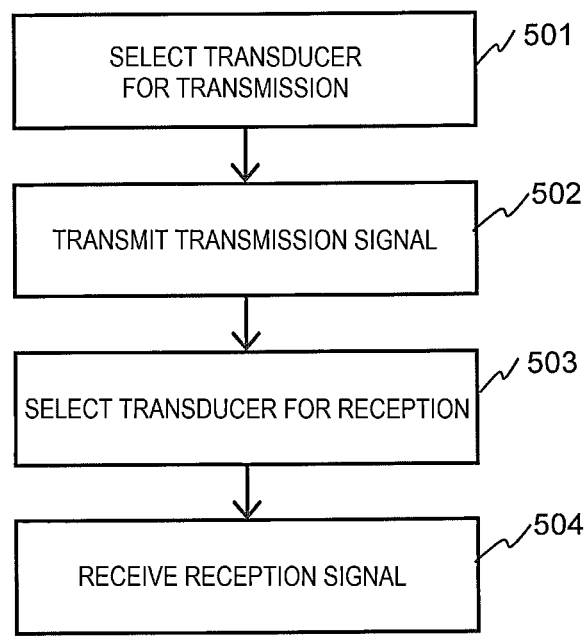

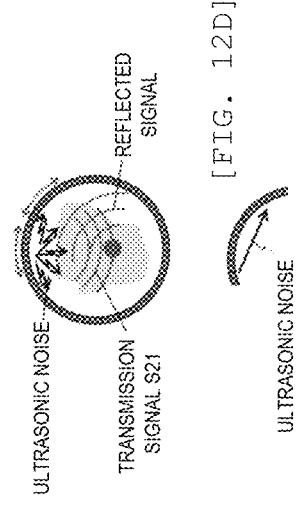
[FIG. 12A]
[FIG. 12B]
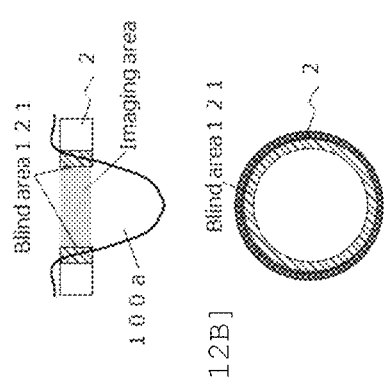
[FIG. 12C]
[FIG. 12D]

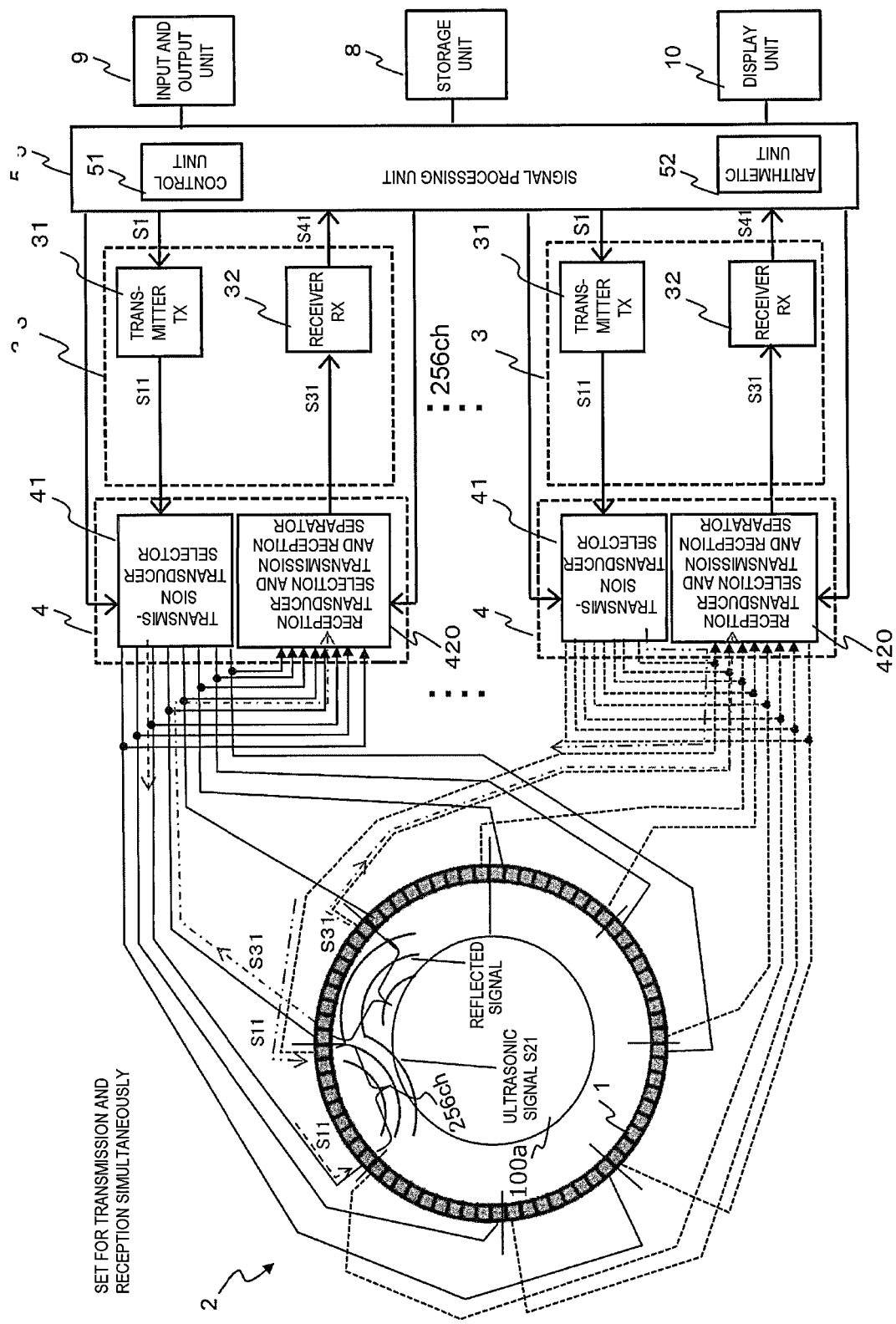
[FIG. 13]

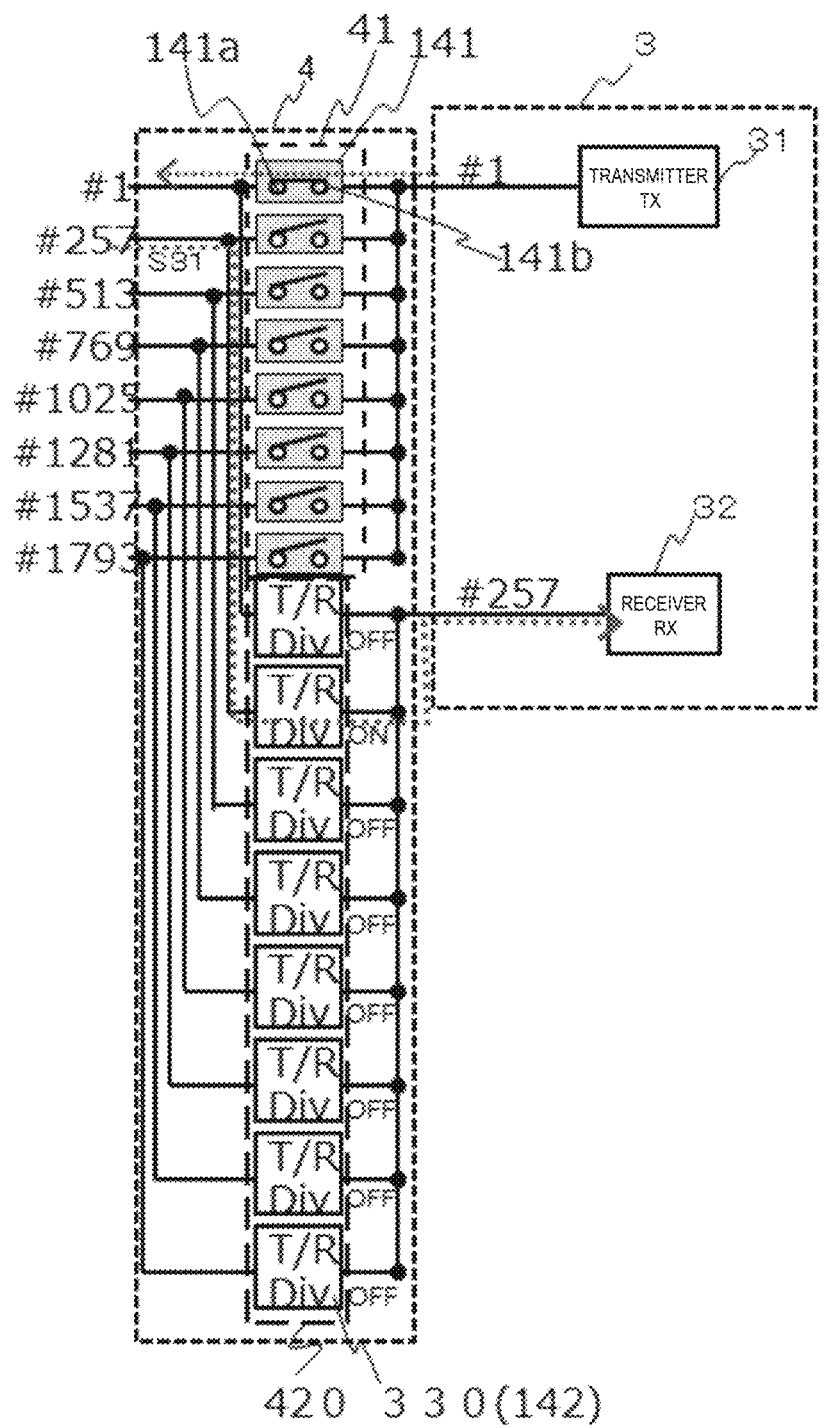
[FIG. 14]

[FIG. 15]
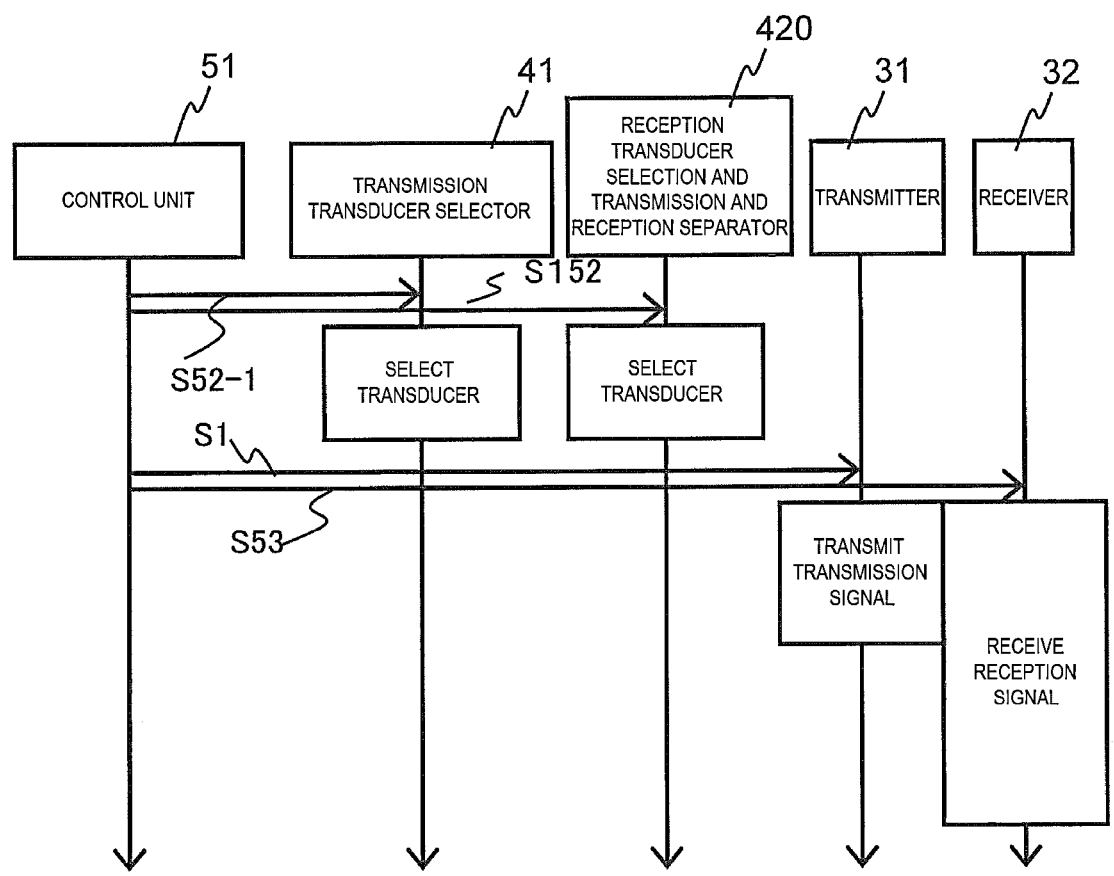

ULTRASONIC CT DEVICE, CONTROL METHOD OF ULTRASONIC CT DEVICE, AND ULTRASONIC TRANSMISSION AND RECEPTION DEVICE

CROSS-REFERENCE TO RELATED APPLICATION

The present application claims priority from Japanese application JP2020-011093, filed on Jan. 27, 2020, the contents of which is hereby incorporated by reference into this application.

TECHNICAL FIELD

The present invention relates to an ultrasonic CT device, in particular to a control method of the ultrasonic CT device.

BACKGROUND ART

PTL 1 discloses an ultrasonic computed tomography (CT) device which is an ultrasonic imaging apparatus in which ultrasonic waves are transmitted from transducers at various positions toward an inside of an object placed in an ultrasonic wave propagation member (such as water) which is a medium that propagates the ultrasonic waves, ultrasonic waves scattered on a surface or the inside of the object or ultrasonic waves passing through the inside of the object are received by the transducers at various positions, and distribution of a physical value (such as sound speed) that reflects a shape and acoustic characteristics of the object is calculated, so that a tomographic image of the object is generated. PTL 1 discloses a configuration in which a transceiver including one transmitter, one receiver and one transmission and reception separator is disposed for each transducer, a transmission signal is output from a transmitter to a transducer, and a reception signal of a transducer is received by a receiver via a transmission and reception separator for processing.

On the other hand, in a general ultrasonic diagnostic device, as in PTL 2, a configuration in which the number of transceivers each including one transmitter, one receiver and one transmission and reception separator is provided smaller than the number of transducers, and the transceivers are selectively connected to any of the transducers by a transducer selection switch is disclosed.

NPL 1 discloses an ultrasonic CT device having a configuration in which when ultrasonic waves are transmitted and received, firstly, a transducer for transmission is selected to transmit the ultrasonic waves, then a transducer for reception is selected to receive the ultrasonic waves.

CITATION LIST

Patent Literature

PTL 1: WO 2017/098641
PTL 2: Japanese Patent No. 4761673

Non-Patent Literature

NPL 1: Compensation of transducer element positions in a ring array ultrasonic computer tomography system (https://iopscience.iop.org/article/10.7567/JJAP.54.07HF24)

SUMMARY OF INVENTION

Technical Problem

In the ultrasonic CT device, the transducers are disposed, for example, in a ring shape so as to surround the object, and therefore, the number of the disposed transducers is larger than that of probes of the general ultrasonic diagnostic device. In an ultrasonic CT device for a breast that is suitable for breast cancer screening or the like, the number of transducers is 2048 channels as an example. On the other hand, in order to miniaturize the device and reduce power consumption, it is desirable to reduce a size of a signal processing circuit, and it is desirable to have a configuration (for example, 256 channels) in which the number of transceivers each including the transmitter, the receiver, and a transmission and reception separation circuit is smaller than the number of transducers.

In such a configuration, when the ultrasonic waves are transmitted to or received from the object, the transducer selection switch connects the transceivers with 256 channels to transducers whose desired number is equal to or less than 256, so that the transmission signal is output from the transmitters to the transducers to transmit the ultrasonic waves. Then, before the ultrasonic waves scattered on the surface of the object or the ultrasonic waves transmitted through the object reach the transducers, the transducer selection switch is instantaneously switched so that the transceivers are connected to the transducers with 256 channels to receive the ultrasonic waves, and the reception signal received by the transducers is received by the receivers via a transmission and reception separation circuit of each transceiver for processing. Transmission and reception operations are repeated a plurality of times until all transducers receive the reception signal. For example, when all transducers are 2048 channels and the number of the transceivers is 256 channels, the transmission and reception are repeated eight times.

However, even if the transducer selection switch is instantaneously switched, the receivers cannot receive the reception signal received by the transducers until the switching is completed. When the object is abreast, a diameter of a tip is small, but a diameter of a base (a part near ribs) is large. Therefore, when the base of the breast is measured with the ultrasonic CT device for a breast, the surface of the breast is disposed close to the ring-shaped transducers. When the object is close to the transducers, a time from the ultrasonic waves being transmitted from the transducers to the ultrasonic waves scattered on the surface of the object coming back to the transducers is extremely short. For this reason, the switching of the transducer selection switch cannot be performed in time, the receivers cannot receive the reception signal from the close object, and a problem arises in that the shape and the distribution of acoustic characteristics of the object disposed close to the transducers cannot be accurately measured.

Further, after the ultrasonic waves are transmitted from the transducers, when the transducer selection switch is switched such that the transceiver is connected to a transducer for reception, electric noise is generated in the transducer selection switch when the transducer selection switch is switched. This electrical noise may reach the receiver of the transceiver that is connected to the transducer selection switch by an electrical circuit. Further, the electric noise generated in the transducer selection switch reaches the transducer connected by the electric circuit, and is transmitted from the transducer as ultrasonic noise. The receiver may receive the reception signal generated by the transducer by receiving the ultrasonic waves resulting from this ultrasonic noise by being scattered by the object or passing through the object. As a result, there is a problem that measurement accuracy of the shape and the distribution of the acoustic characteristics of the object is reduced.

An object of the invention is to provide an ultrasonic CT device in which a reflected signal or the like from an object disposed close to transducers is received, and a reception signal thereof can be received by a receiver while transceivers whose number is smaller than the number of the transducers are used.

Solution to Problem

In order to solve the above problem, an ultrasonic CT device according to the invention includes: a transducer array in which a plurality of transducers are arranged; transceivers whose number is smaller than the number of the transducers; and a transducer selector disposed for each of the transceivers. The transceivers each include a transmitter configured to transmit a transmission signal to the transducer, and a receiver configured to receive a reception signal received by the transducer. The transducer selector includes a transmission transducer selector and a reception transducer selector. The transmission transducer selector is configured to selectively connect the transmitter to any of the transducers in the transducer array, and the reception transducer selector is independent of the transmission transducer selector, and is configured to selectively connect the receiver to any of the transducers in the transducer array. The transmission transducer selector and the reception transducer selector respectively connect a transmitter and a receiver in one transceiver to the same or different transducers simultaneously.

Advantageous Effect

According to the invention, a transmitter and a receiver in one transceiver can be simultaneously connected to the same or different transducers before ultrasonic waves are transmitted, so that simultaneously with the start of the transmission of the ultrasonic waves, reception of the ultrasonic waves can be started, and a reflected signal from a subject disposed close to the transducers can also be received.

BRIEF DESCRIPTION OF DRAWINGS

FIG. 1 is a block diagram showing an overall configuration of an ultrasonic CT device according to a first embodiment of the invention.

FIG. 2 is a functional block diagram of the ultrasonic CT device according to the first embodiment.

FIG. 3 is a block diagram showing a circuit configuration of a transducer selector 4 of the ultrasonic CT device according to the first embodiment.

FIG. 4 is a flowchart showing operations of the ultrasonic CT device according to the first embodiment.

FIGS. 5A and 5B are flowcharts showing a part of the operations of the ultrasonic CT device according to the first embodiment.

FIG. 6 is a diagram showing an operation sequence of the ultrasonic CT device according to the first embodiment.

FIGS. 7A to 7F are diagrams showing a region (Tx) of a transducer used for transmission and a region (Rx) of a transducer used for reception for each imaging view of the ultrasonic CT device according to the first embodiment.

FIG. 8 is a diagram showing functional blocks and a signal flow at the time of transmission of an ultrasonic CT device according to a comparative example.

FIG. 9 is a diagram showing functional blocks and a signal flow at the time of reception of the ultrasonic CT device according to the comparative example.

FIGS. 10A and 10B are block diagrams respectively showing settings at the time of transmission and reception of a transducer selector 40 of the ultrasonic CT device according to the comparative example.

FIG. 11 is a flowchart showing operations of the ultrasonic CT device according to the comparative example.

FIGS. 12A and 12B are a longitudinal sectional view and a cross sectional view showing a blind area 121 of the ultrasonic CT device according to the comparative example, FIG. 12C is an explanatory diagram showing occurrence of ultrasonic noise due to electrical switching noise, and FIG. 12D is an explanatory diagram showing an example in which ultrasonic noise is directly received by another transducer.

FIG. 13 is a functional block diagram of an ultrasonic CT device according to a second embodiment.

FIG. 14 is a block diagram showing a circuit configuration of a transducer selector 4 of the ultrasonic CT device according to the second embodiment.

FIG. 15 is a diagram showing an operation sequence of the ultrasonic CT device according to the second embodiment.

DESCRIPTION OF EMBODIMENTS

An ultrasonic CT device according to one embodiment of the invention will be described.

First Embodiment

In a first embodiment of the invention, an ultrasonic CT device for a breast will be described. As shown in FIGS. 1 and 2, the ultrasonic CT device for a breast according to the present embodiment includes a bed 101 on which a subject 100 is placed facing downward, and a measurement unit 102 disposed below an opening provided in the bed 101. The measurement unit 102 includes a container 103 filled with water, a transducer array 2, a transceiver 3, a transducer selector 4, a signal processing unit 5, a mechanism unit 6 for vertically moving the transducer array 2, and a drive unit 7 of the mechanism unit 6. The container 103 filled with the water is fixed to the bed 101 so that an opening of the container 103 matches the opening of the bed 101, and a breast 100a of the subject 100 is inserted therein. The transducer array 2 is disposed inside or outside the container 103.

The transducer array 2 has a configuration in which a plurality of transducers 1 are arranged, and here has a ring shape as shown in FIG. 2. The number of the transducers 1 is, for example, 2048 channels. The number of the transceivers 3 is smaller than the number of the transducers 1, and is, for example, 256 channels. The transducer selector 4 is disposed for each of the transceivers 3.

Each of the transceivers 3 includes a transmitter 31, a receiver 32, and a transmission and reception separator 33. In the signal processing unit 5, a control unit 51 and an arithmetic unit 52 are disposed. The control unit 51 outputs an electric signal S1 to the transmitter 31, and controls operations of the transducer selector 4. The arithmetic unit 52 generates an ultrasonic CT image by performing arithmetic processing on a reception signal S41 output from the receiver 32. The signal processing unit 5 is connected to an input and output unit 9 for receiving imaging conditions and the like from a user, a storage unit 8, and a display device 10 for displaying the generated CT image and the like.

The transmitter 31 receives the electric signal S1 transmitted from the control unit 51, amplifies the signal to generate a transmission signal S11, and outputs the transmission signal S11 to the transducer 1 connected via the transducer selector 4. The transducer 1 that receives the transmission signal S11 converts the transmission signal S11 into an ultrasonic signal S21 and transmits the ultrasonic signal S21 to a space where the breast 100a is disposed. The ultrasonic signal S21 is partially scattered and reflected by the breast 100a, while another part is transmitted through the breast 100a and reaches a plurality of transducers 1 of the transducer array 2, and is converted into a reception signal S31, which is an electric signal, by the transducers 1.

The receiver 32 receives the reception signal S31 received by the transducer 1 via the transducer selector 4 and outputs a reception signal S41 obtained by amplification or the like to the arithmetic unit 52. The transmission and reception separator 33 prevents the transmission signal S11 output from the transmitter 31 from being input to the receiver 32 due to reflection or the like. For example, the transmission and reception separator 33 is configured to reflect a signal (transmission signal S11) having a signal value equal to or larger than a threshold value, and pass a signal (reception signal S31) having a signal value smaller than the threshold value.

Since the number of the transmitters 31 and the receivers 32 (for example, 256 ch) is smaller than the number of the transducers 1 (2048 ch), the transducer selector 4 selectively connects the transmitters 31 and the receivers 32 to any of the transducers 1 separately, so that the ultrasonic signal is transmitted from the transducers 1 whose number is equal to or less than 256 ch and connected to the transmitters 31, and the receivers 32 receive the reception signal received by the transducers 1 whose number is equal to or less than 256 ch.

In the present embodiment, the transducer selector 4 includes a transmission transducer selector 41 and a reception transducer selector 42. Under the control of the control unit 51, the transmission transducer selector 41 selectively connects the transmitter 31 to a transducer 1, among the transducers of the transducer array 2, from which ultrasonic waves are to be transmitted. Under the control of the control unit 51, the reception transducer selector is independent of the transmission transducer selector 41, and is configured to selectively connect the receiver 32 to a transducer 1, among the transducers of the transducer array 2, by which the ultrasonic waves are to be received. With such a configuration, the transmission transducer selector 41 and the reception transducer selector 42 allow the transmitter 31 and the receiver 32 in one transceiver 3 to be simultaneously connected to the same or different transducers 1 separately.

Therefore, before the transmission signal S11 is transmitted from the transmitter 31, selective connection between the receiver 32 and the transducer 1 can be completed, so that a reflected signal of the ultrasonic waves can be received from a beginning of the transmission of the ultrasonic signal S21. Therefore, with such a configuration including a number of transceivers 3 less than a number of transducers 1, the reflected signal or the like from an object (breast 100a) disposed close to the transducer 1 is received, and the reception signal thereof can be received by a receiver, and the reception signal from the object (breast 100a) disposed close to the transducer array 2 can be received by the receiver 32. Further, since there is no need to switch the transducer selector 4 for reception between transmission and reception, electric noise does not occur due to the switching, and the arithmetic unit 52 can generate an ultrasonic CT image with low noise based on the reception signal with low noise.

A configuration of the transducer selector 4 will be further described. As shown in FIG. 3, the transmission transducer selector 41 and the reception transducer selector 42 in one transducer selector 4 are each provided with a number of (8) switches 141, 142, the number being obtained by dividing the number of the transducers 1 (here, 2048 ch) constituting the transducer array 2 by a total number of the transceivers 3 (here, 256 ch). As shown in FIG. 3, eight predetermined transducers 1 (in the example of FIG. 3, 1st, 257th, 513th, 769th, 1025th, 1281st, 1537th, 1793th) are connected to terminals 141a which is one end of the switches 141 of the transmission transducer selector 41, and a transmitter 31 is connected to terminals 141b which is the other end of the switches 141. By turning on only one of the switches 141 and turning off the others, the transducers 1 connected to the turned-on switch 141 can be selectively connected to the transmitter 31. On the other hand, as shown in FIG. 3, eight predetermined transducers 1 (in the example of FIG. 3, 1st, 257th, 513th, 769th, 1025th, 1281st, 1537th, 1793th) are connected to terminals 142a which is one end of the switches 142 of the reception transducer selector, and the receiver 32 is connected to terminals 142b which is the other end of the switches 142. By turning on only one of the switches 142 and turning off the others, the transducers 1 connected to the turned-on switch 142 can be selectively connected to the receiver 32.

Therefore, before the transmission signal S11 is transmitted from the transmitter 31 to the transducer 1, the control unit 51 selectively turns on one of the switches 141 of the transmission transducer selector 41 connected to one transceiver 3, and meanwhile, selectively turns on one of the switches 142 of the reception transducer selector 42, so as to allow the transmitter 31 and the receiver 32 to be simultaneously connected to the same or different transducers 1 separately. Then, the transmission signal is transmitted from the transmitter 31 to the transducers 1, and the ultrasonic signal is transmitted to the subject 100, so that simultaneously with the transmission, the receiver 32 can receive the reception signal of the transducer already connected to the receiver 32. Therefore, even when the breast 100a is close to the transducer 1 that transmits the ultrasonic signal S21, the reflected signal or the like can be received by the same transducer as the transducer 1 that performs transmission or a transducer in an immediate vicinity of the transducer, and be passed to the receiver 32.

Therefore, the receiver 32 can start receiving the reception signal immediately after the ultrasonic signal S21 is transmitted. Specifically, the receiver 32 can start receiving the reception signal even during the ultrasonic signal S21 is transmitted.

Next, operations of each unit when three-dimensional information of the breast 100a is obtained by obtaining tomographic images of the breast 100a at a plurality of depth positions with the use of the ultrasonic CT device for a breast according to the present embodiment will be described by using flowcharts of FIGS. 4 and 5, a sequence diagram of FIG. 6, and view diagrams of FIG. 7. Here, an example in which a reflected wave image of the breast 100a is captured will be described as an example.

The transceiver 3 and the signal processing unit 5 are configured with a computer or the like including a processor, such as a central processing unit (CPU) or a graphics processing unit (GPU), and a memory, and the CPU reads and executes a program stored in the memory, such that functions of respective units of the transceiver 3 and the signal processing unit 5 can be implemented by software, and a part or all of the functions can be implemented by hardware. For example, the transceiver 3 and the signal processing unit 5 are configured by using a custom IC such as an application specific integrated circuit (ASIC) or a programmable IC such as a field-programmable gate array (FPGA), such that a circuit may be designed so as to implement the functions of the respective units of the transceiver 3 and the signal processing unit 5.

Firstly, the control unit 51 receives imaging conditions of the ultrasonic CT device from the user through the input and output unit 9. The control unit 51 stores the set conditions and the like in the storage unit 8.

When the subject 100 is placed facing downward on the bed 101, the breast 100*a* is inserted into the container 103, and the control unit 51 receives an instruction of starting imaging from the user via the input and output unit 9, the control unit 51 selects the transducer 1 used for transmission and the transducer 1 used for reception (Step 401). As shown in the sequence diagram of FIG. 6, the operation of the control unit 51 in Step 401 is firstly outputting a control signal S51 for turning on an operation to the transmission and reception separator 33. Thereafter or at the same time, control signals 52-1, 52-2 for selecting one switch 141 and one switch 142 are respectively output to the transmission transducer selector 41 and reception transducer selector 42. Thereby, for example, as shown in FIG. 7(*a*), the ring-shaped transducer array 2 (for example, 2048 ch) is divided into eight parts, and the transmitters 31 of the transceivers 3 are connected to the respective transducers 1 in the same number (for example, 256 ch) of the transceivers 3 in a region (Tx) via the transmission transducer selector 41. Further, as shown in FIG. 7(*a*), the receivers 32 of the transceivers 3 are connected to respective transducers 1 in a region (Rx: 256 ch) on a left side of the region (Tx) of the transducer array 2 via the reception transducer selector 42.

Next, the control unit 51 causes the transducer 1 in the region (Tx) to transmit the ultrasonic signal S21, and the ultrasonic wave that reaches the transducer in the region (Rx) is received by the receiver 32 as the reception signal (Step 402). Specifically, as shown in the sequence diagram of FIG. 6, the control unit 51 transmits the electric signal S1 to each transmitter 31. As a result, the transmitter 31 amplifies the electric signal S1 to generate the transmission signal S11, and outputs the transmission signal S11 to the transducer 1 in the region (Tx) connected via the transmission transducer selector 41. The transducer 1 converts the transmission signal S11 into the ultrasonic signal S21 and transmits the ultrasonic signal S21. Further, the control unit 51 outputs a signal S53 instructing each receiver 31 to receive the reception signal. As a result, the receiver 32 receives the reception signal output from the transducer 1 in the region (Rx), amplifies the signal, and outputs the amplified signal to the arithmetic unit 52. The arithmetic unit 52 stores the signal in the storage unit 8.

At this time, as shown in FIG. 5A, after the transmission of the ultrasonic signal S21 is completed, the reception of the ultrasonic wave reflected by the breast 100*a* may be started (Steps 402-1, 402-2), and as shown in FIG. 5B, the reception may be started simultaneously with a start of the transmission of the ultrasonic wave (Step 402). This is an operation that can be implemented by a configuration in which the transmission transducer selector 41 and the reception transducer selector of the present embodiment can separately select the transducers at the same time.

The above Steps 401, 402 are sequentially repeated in each view of FIGS. 7A to 7F (Step 403). In the three views of FIGS. 7A to 7F, positions of the region (Tx) for transmitting the ultrasonic signal S21 are the same. In the three views in FIGS. 7D to 7F, positions of the region (Tx) for transmitting the ultrasonic signal S21 are the same, and for the views of FIGS. 7A to 7C, the positions are shifted clockwise by half of 256 channels (128 ch). In the views of FIGS. 7B and 7E, the region (Tx) for transmitting the ultrasonic signal 21 and the region (Rx) for receiving the ultrasonic signal 21 are the same.

The arithmetic unit 52 performs processing on the reception signals obtained in each view, so as to generate a cross-sectional image (reflected wave image) of the breast 100*a* by a known method (Step 404).

By repeating the above Steps 401 to 404 while changing a position of the transducer array 2 at a predetermined pitch in a depth direction, the tomographic images of the breast 100*a* are generated at all predetermined depths (Steps 405, 406). Thereby, the three-dimensional data of the breast 100*a* can be obtained.

Comparative Example

Here, an ultrasonic CT device of a comparative example will be described with reference to FIGS. 8 to 11.

In the ultrasonic CT device of the comparative example, a configuration of a transducer selector 40 is different from that of the transducer selector 4 of the first embodiment. As shown in FIGS. 8 and 9, the transducer selector 40 is not divided into the transmission transducer selector 41 and the reception transducer selector 42, and as shown in FIGS. 10A and 10B, the transducer 1 is selected by eight switches 140 both at the time of transmission and at the time of reception. Specifically, as shown in FIGS. 8 and 10A, at the time of transmission, one of the switches 140 of the transducer selector 40 is turned on, and one transducer 1 (for example, the first transducer) is connected to the transmitter 31. Further, as shown in FIGS. 9 and 10B, at the time of reception, one of the switches 140 of the transducer selector 40 is switched to on, and one transducer 1 (for example, a 257th transducer) is connected to the receiver 32. Other configurations are the same as those in the first embodiment.

In the ultrasonic CT device of the comparative example, as shown in a transmission and reception operation in the flowchart of FIG. 11, after one transducer 1 for transmission is selectively connected to the transmitter 31 by the transducer selector 40 before transmission (Step 501), a transmission signal is transmitted from the transmitter 31 to the transducer 1 to transmit the ultrasonic signal (Step 502). Next, after the transducer selector 40 is switched and the transducer 1 for reception is selectively connected to the receiver 32 (Step 503), the reception signal of the transducer 1 is received by the receiver 32 (Step 504).

That is, the transmission and reception operation of the comparative example is different from the flows shown in FIGS. 5A and 5B according to the first embodiment, and if the operation of switching the transducer selector 40 to connect the transducer for reception to the receiver 32 is not performed after the ultrasonic signal is transmitted, the receiver 32 cannot receive the reception signal. Therefore, in the ultrasonic CT device of the comparative example, even if the transducer selector 40 is instantaneously switched after the ultrasonic signal is transmitted, the receiver 32 cannot receive the reception signal received by the transducer 1 for reception until the switching is completed. Therefore, in the ultrasonic CT device of the comparative example, as shown in FIGS. 12A and 12B, reflected waves that are reflected on a surface of the breast close to the transducer array 2 and reach the transducer in a very short time cannot be received by the receiver 32, and a blind area 121 where an image cannot be acquired is generated.

Further, as shown in FIG. 12C, in the device of the comparative example, after the ultrasonic wave is transmitted from the transducer, since the transducer selector 40 is switched to connect the receiver 32 to the transducer for reception, the electric noise is generated when the transducer selector 40 is switched. This electric noise may reach the receiver 32 as the electric signal and affect the generated tomographic images.

When the electric noise reaches the transducer 1 connected to the transducer selector 40, the electric noise is transmitted from the transducer as the ultrasonic noise. This ultrasonic noise, as shown in FIG. 12D, may be directly received by another transducer having sensitivity in a direction of the transducer 1 that transmits the ultrasonic noise. Energy of the ultrasonic signal which is directly received is larger than energy of the ultrasonic signal reflected or scattered by the breast 100a, and therefore affects the generated tomographic images.

Compared with such a comparative example, the ultrasonic CT device according to the first embodiment has the configuration in which the transducer selector 40 is divided into the transmission transducer selector 41 and the reception transducer selector 42, so that before transmission, both the transducer 1 for transmission and the transducer 1 for reception can be respectively connected to the transmitter 31 and the receiver 32. Therefore, even when the ultrasonic wave is transmitted to the surface of the breast 100a disposed close to the transducer array 2, the reflected signal reaching another transducer 1 in a very short time can be received, and the blind area 121 is not generated. In addition, there is no need to switch the transducer selector 40 between the transmission and the reception, and there is an advantage that the electric noise is not generated.

Second Embodiment

Hereinafter, an ultrasonic CT device for a breast according to the second embodiment will be described with reference to FIGS. 13 to 15.

The ultrasonic CT device for a breast according to the second embodiment has the same configuration as the device according to the first embodiment, but is different from the first embodiment in that the transmission and reception separator 33 according to the first embodiment also serves as the switch 142 that configures the reception transducer selector 42.

Specifically, a transmission and reception separator 330 having a switch function is adopted in the second embodiment, and configures a reception transducer selection and transmission and reception separator 420 as shown in FIGS. 13 and 14 instead of the switches 142 of the reception transducer selector 42.

The transmission and reception separator 330 having the switch function includes, for example, a diode bridge circuit in which a bridge circuit is configured with a plurality of semiconductor diodes, and is configured to be switched between a short circuit state and an open state by switching magnitude of a voltage applied to the diode from a midpoint of an arm. In such a transmission and reception separator 330, a small signal (reception signal) passes when being in the short circuit state, while a large signal (transmission signal) is blocked (significantly attenuates), and when being in the open state, both the small signal and the large signal are blocked (significantly attenuates).

The control unit 51 outputs a control signal S152 for switching a signal of the voltage applied to the diode of the transmission and reception separator 330 constituting the reception transducer selection and transmission and reception separator 420 as shown in FIG. 15, such that only the transmission and reception separator 330 connected to the transducer for receiving the reception signal is short-circuited, and another transmission and reception separator 330 is opened. Therefore, the transducer 1 for reception can be selected, and the transmission signal and the reception signal can be separated.

Other configurations and operations of the ultrasonic CT device for a breast of the second embodiment are the same as the configurations and operations of the first embodiment, and thus description thereof is omitted.

In the ultrasonic CT device for a breast according to the second embodiment, since the reception transducer selection and transmission and reception separator 420 serves as both a transmission and reception separator and a transducer selector, a scale of the circuit can be reduced and the device can be miniaturized.

In the first and second embodiments described above, the number of switches 141 of the transmission transducer selector 41 may be different from the number of the switches 141 of the reception transducer selector 42 or the switch 141 of the reception transducer selection and transmission and reception separator 420 or the number of the transmission and reception separators 330 having the switch function. For example, more receivers 32 are disposed in the transceiver 3 than the transmitters 31, and more transducers 1 than the transducer used for the transmission may be connected to the receiver 32 by the switches 141 or the transmission and reception separator 330 having the switch function to receive and process the reception signal. As a result, a CT image can be generated by using a large number of reception signals, so that image accuracy can be improved.

REFERENCE SIGN LIST 2 transducer array, 3 transceiver, 4, 40 transducer selector, 5 signal processing unit, 6 mechanism unit, 7 drive unit, 8 storage unit, 9 input and output unit, 10 display device, 31 transmitter, 32 receiver, 33 transmission and reception separator, 51 control unit, 52 arithmetic unit, 100 subject, 100a breast, 101 bed, 102 measurement unit, 103 container, 141, 142 switch, 330 transmission and reception separator, 420 reception transducer selection and transmission and reception separator

The invention claimed is:
1. An ultrasonic CT device comprising:
a transducer array in which a plurality of transducers are arranged;
a plurality of transceivers whose number is smaller than the number of the transducers; and
a transducer selector disposed for each of the transceivers, wherein
the transceivers each include a transmitter configured to transmit a transmission signal to the transducer, and a receiver configured to receive a reception signal received by the transducer,
the transducer selector in each of the transceivers includes a transmission transducer selector and a reception transducer selector, the transmission transducer selector in each of the transceivers is configured to selectively connect a corresponding transmitter of a corresponding transceiver to any one of the transducers in the transducer array, the reception transducer selector in each of the transceivers is independent of the transmission transducer selector in each of the transceivers, and is configured to selectively connect a corresponding receiver of the corresponding transceiver to any one of the transducers in the transducer array, and a first transmission transducer selector and a first reception transducer selector of a first transceiver respectively connect a first transmitter and a first receiver in the first transceiver to the same or different transducers before a transmission signal is transmitted from the first transmitter.

2. The ultrasonic CT device according to claim 1, further comprising:

a control unit configured to control operation of the transmission transducer selector and the reception transducer selector in each of the transceivers, wherein the control unit controls the transmission transducer selector and the reception transducer selector in each of the transceivers separately, such that the transmitter in each of the transceivers is connected to a transducer to transmit an ultrasonic wave, and the receiver in each of the transceivers is connected to a transducer to receive an ultrasonic wave.

3. The ultrasonic CT device according to claim 1, wherein the transmission transducer selector and the reception transducer selector, in each of the transceivers, each include a number of switches, the number being obtained by dividing the number of the transducers constituting the transducer array by a total number of the transceivers, any one of the transducers is connected to a switch of any one of the transmission transducer selectors in the transceivers, any one of the transducers is connected to a switch of any one of the reception transducer selectors in the transceivers, and the control unit performs control such that before the transmission signal is transmitted from the first transmitter, one of the switches of the first transmission transducer selector is selectively turned on, and one of the switches of the first reception transducer selector is selectively turned on, and then, the transmission signal is transmitted from the first transmitter.

4. The ultrasonic CT device according to claim 2, wherein the first receiver starts receiving the reception signal immediately after the ultrasonic wave is transmitted from a transducer connected to the first receiver.

5. The ultrasonic CT device according to claim 2, wherein the receiver starts receiving the reception signal during the transmission of the ultrasonic wave from a transducer connected to the first receiver.

6. The ultrasonic CT device according to claim 1, wherein a transmission and reception separator is disposed between the receiver and the reception transducer selector in each of the transceivers.

7. The ultrasonic CT device according to claim 1, wherein the reception transducer selector in each of the transceivers also serves as a transmission and reception separator which is configured to separate the transmission signal and the reception signal and passes only the reception signal.

8. The ultrasonic CT device according to claim 3, wherein the number of the switches of the transmission transducer selector in each of the transceivers is different from the number of the switches of the reception transducer selector in each of the transceivers.

9. The ultrasonic CT device according to claim 1, wherein the transducer array has a shape in which a part of transducers is disposed at positions where ultrasonic waves transmitted from another part of transducers are able to be directly received.

10. The ultrasonic CT device according to claim 9, wherein the transducer array has a ring shape.

11. A control method of an ultrasonic CT device, the ultrasonic CT device including:

a transducer array in which a plurality of transducers are arranged;

a plurality of transceivers whose number is smaller than the number of the transducers; and a transmission transducer selector and a reception transducer selector disposed for each of the transceivers, the control method of the ultrasonic CT device comprising the steps of:

selectively connecting a corresponding transmitter included in a corresponding transceiver to any of the transducers in the transducer array by the transmission transducer selector in each of the transceivers; and selectively connecting a corresponding receiver included in the corresponding transceiver to any of the transducers in the transducer array by the reception transducer selector in each of the transceivers;

wherein a first transmission transducer selector and a first reception transducer selector of a first transceiver respectively connect a first transmitter and a first receiver in the first transceiver to the same or different transducers before a transmission signal is transmitted from the first transmitter.

12. The control method of the ultrasonic CT device according to claim 11, wherein:

after the transducers are selectively and separately connected to the transmitter and the receiver by the transmission transducer selector and the reception transducer selector of the transceivers, an ultrasonic wave is transmitted from the corresponding transmitter to a transducer connected therewith, and a reception signal from the transducer that receives the ultrasonic wave is received by the corresponding receiver connected to the transducer.

13. An ultrasonic transmission and reception device, comprising:

a plurality of transceivers whose number is smaller than the number of transducers included in a transducer array connected therewith; and a transducer selector disposed for each of the transceivers, wherein the transceivers each include a transmitter configured to transmit a transmission signal to the transducer, and a receiver configured to receive a reception signal received by the transducer, the transducer selector in each of the transceivers includes a transmission transducer selector and a reception transducer selector, the transmission transducer selector in each of the transceivers is configured to selectively connect a corresponding transmitter of a corresponding transceiver to any one of the transducers in the transducer array, the reception transducer selector in each of the transceivers is independent of the transmission transducer selector in each of the transceivers, and is configured to selectively connect a corresponding receiver of a corresponding transceiver to any one of the transducers in the transducer array, and a first transmission transducer selector and a second reception transducer selector of a first transceiver respectively connect a first transmitter and a first receiver in the first transceiver to the same or different transducers before a transmission signal is transmitted from the first transmitter.

* * * * *